United States Patent [19]
Redano

[11] Patent Number: 5,947,901
[45] Date of Patent: Sep. 7, 1999

[54] METHOD FOR HEMODYNAMIC STIMULATION AND MONITORING

[76] Inventor: Richard T. Redano, 2605 Werlein St., Houston, Tex. 77005

[21] Appl. No.: 08/926,209

[22] Filed: Sep. 9, 1997

[51] Int. Cl.⁶ ........................................................ A61B 8/00
[52] U.S. Cl. ............................ 600/439; 600/454; 600/38; 601/2; 601/46
[58] Field of Search .................................... 601/2, 46, 53; 600/38, 439, 438, 454, 455; 128/898

[56] References Cited

U.S. PATENT DOCUMENTS

| | | |
|---|---|---|
| 2,283,285 | 5/1942 | Pohlman ........................................ 601/2 |
| 3,499,437 | 3/1970 | Balamuth ...................................... 601/2 |
| 3,735,756 | 5/1973 | Richards et al. . |
| 3,744,486 | 7/1973 | Wilson ........................................ 600/38 |
| 4,073,289 | 2/1978 | Fahim ........................................... 601/2 |
| 4,127,118 | 11/1978 | Latorre . |
| 4,309,989 | 1/1982 | Fahim ........................................... 601/2 |
| 4,334,543 | 6/1982 | Fehr . |
| 4,484,569 | 11/1984 | Driller et al. . |
| 4,542,753 | 9/1985 | Brenman et al. . |
| 4,580,570 | 4/1986 | Sarrell et al. . |
| 4,585,005 | 4/1986 | Lue et al. . |
| 4,612,937 | 9/1986 | Miller . |
| 4,663,102 | 5/1987 | Brenman et al. . |
| 4,757,820 | 7/1988 | Itoh . |
| 4,829,991 | 5/1989 | Boeck ........................................ 600/38 |
| 5,000,185 | 3/1991 | Yock . |
| 5,062,430 | 11/1991 | Bonnefous . |
| 5,067,480 | 11/1991 | Woog et al. ................................. 601/46 |
| 5,236,904 | 8/1993 | Gerstenberg et al. . |
| 5,242,391 | 9/1993 | Place et al. . |
| 5,413,550 | 5/1995 | Castel ............................................ 601/3 |
| 5,462,059 | 10/1995 | Ferrera et al. . |
| 5,482,039 | 1/1996 | Place . |
| 5,571,118 | 11/1996 | Boutos . |
| 5,578,060 | 11/1996 | Pohl et al. . |
| 5,630,837 | 5/1997 | Crowley . |

OTHER PUBLICATIONS

Memorial Urology Associates, "Peyronie's Disease", 1997.
Mettler Electronics Brochure entitled "Sys*Stim 220" May 1992.
Physio Technology Inc. Brochure entitled "Omnisound" 1986.

Primary Examiner—Ruth S. Smith

[57] ABSTRACT

The present invention is directed toward a method for stimulating and/or monitoring hemodynamic activity, such as blood flow, in a penis. The method of the present invention comprises the coupling of an ultrasound source to the outer surface of the penis and transmitting ultrasound energy into the penis at a sufficient frequency and intensity to increase hemodynamic activity. An apparatus is also provided for practicing the method of the present invention. The apparatus provides for position adjustment of the ultrasound transducers during the circumferential expansion of the penis resulting from increased hemodynamic activity.

17 Claims, 3 Drawing Sheets

METHOD FOR HEMODYNAMIC STIMULATION AND MONITORING

BACKGROUND OF THE INVENTION

1. Field of the Invention

The present invention is directed toward a method and apparatus for stimulating and/or monitoring hemodynamic activity, such as blood flow, in a penis. The method of the present invention comprises the coupling of an ultrasound source to the outer surface of the penis and transmitting ultrasound energy into the penis at a sufficient frequency and intensity to increase hemodynamic activity. An apparatus is also provided for practicing the method of the present invention. The apparatus provides for position adjustment of the ultrasound transducers during the circumferential expansion of the penis resulting from increased hemodynamic activity.

2. Description of the Prior Art

Erectile dysfunctionality may result from neurogenic, vasculogenic, hormonal, and/or psychogenic causes. The term "erectile dysfunctionality", as used herein, refers to the inability or impaired ability of a male patient to experience a penile erection. The urological arts have devised a number of therapies for treating erectile dysfunctionality. These therapies include psychological, pharmacological, and electrical therapies.

A method and device for electrically stimulating a penile erection is disclosed in U.S. Pat. No. 4,585,005 to Lue et al. The method disclosed in Lue includes the implantation of an electrode on the cavernous nerve. The electrodes of Lue are connected to a receiver that is subcutaneously implanted in the patient. The method and device disclosed in Lue requires surgery. Additionally, if the device disclosed in Lue malfunctions, surgery is required to remove it. Surgery is expensive and time consuming. Additionally, many patients may have emotional or psychological aversions to having electrodes implanted in their penis.

An apparatus for electrically stimulating penile tissue to cause a penile erection is disclosed in U.S. Pat. No. 5,571,118 to Boutos. Boutos discloses the use of a ring having a conductive surface that is placed on the penis and/or the scrotum. There is a risk that such a device may short circuit, if used in an electrically conductive environment, such as a hot tub. This is a major drawback of external electrical therapies, as contrasted with external ultrasound therapies. The use of ultrasound transducers on submerged patients has been applied in other nonanalogous arts, such as extracorporeal shock wave lithotripsy.

An apparatus for electrically stimulating a penile erection is disclosed in U.S. Pat. Nos. 4,542,753 and 4,663,102 to Brennan et al. Brennan discloses a body member for insertion into the rectum of a patient. The body member comprises surface mounted electrodes. Brennan teaches insertion of the body member sufficiently deep into the patient for at least one electrode to contact the prostate gland. The device disclosed by Brennan is highly invasive. Patients may experience physical discomfort from the rectal insertion of the device disclosed in Brennan.

Pharmacological therapies for erectile dysfunctionality include the injection of drugs into the penis. Such methods are disclosed in U.S. Pat. No. 5,236,904 to Gerstengerg et al. and U.S. Pat. No. 4,127,118 to Latorre. Many male patients find the thought of jabbing a hypodermic needle into their penis to be discomforting. Penile injections may also result in the buildup of scar tissue, bleeding, and persistent prolonged erection (priapism). The unacceptability of therapies requiring the intracavernosal injection of drugs into the penis is well documented in the urological arts (See U.S. Pat. No. 5,482,039 to Place et al.; and Padma-Nathan, *Treatment of Men With Erectile Dysfunction With Transurethral Alprostadil,* The New England Journal of Medicine, 336:1–7, Jan. 2, 1997).

Other pharmacological therapies for erectile dysfunctionality include delivering a drug directly into the urethra of a patient. Methods and devices for transurethral delivery of drugs into the penis are disclosed in U.S. Pat. Nos. 5,242,391 and 5,482,039 to Place et al. These transurethral drug delivery methods involve inserting a shaft into the urethra. The insertion of a shaft up the urethra may cause discomfort in many patients or be objectionable for many of the same reasons that penile hypodermic needle injections are objectionable.

The present invention provides an ultrasonic therapy for hemodynamic stimulation of the penis that does not require (1) the injection of drugs into the penis, (2) surgical implantation of electrodes into the penis, or (3) the insertion of electrodes into the rectum. The method of the present invention may be practiced in an electrically conductive medium without the short circuiting risk present in prior art methods of electrotherapy for erectile dysfunctionality.

SUMMARY OF THE INVENTION

Blood is the hydraulic driving fluid that provides the mass increase and force which result in a penile erection. Under normal conditions, a penile erection occurs when the mass flow rate of blood into the penis exceeds the mass flow rate of blood out of the penis for a certain time interval. Vasculogenic erectile dysfunctionality may result from a restriction or blockage of blood flow into the penis or from excess blood flow out of the penis. The present invention is aimed at treating vasculogenic erectile dysfunctionality that results from inadequate blood flow into the penis. The present invention may also be used with devices intended to restrict the venous outflow of blood from the penis, such as the venous flow controller sold under the trademark ACTIS by Vivus, Inc. of Menlo Park, Calif.

The present invention provides a method for stimulating hemodynamic activity within a penis. The first method step of the present invention is coupling an ultrasound source to the outer surface of a penis. The second method step of the present invention is transmitting ultrasound energy into the penis at a sufficient frequency and intensity to increase hemodynamic flow within the penis.

A portion of the ultrasound energy transmitted into the body is converted to thermal energy. The increased blood flow resulting from the use of the present invention provides a thermal transport medium for transporting and dispersing thermal energy introduced from the transmission of ultrasound energy. This thermal transport helps to minimize localized temperature increases within the penis.

The present invention also provides a method for monitoring the effect of the stimulation therapy of the present invention. The present invention also includes ultrasonographically measuring one or more hemodynamic parameters within the penis. These hemdynamic parameters may include blood flow velocity, blood pressure, and/or blood temperature. The measured hemodynamic parameters can be graphically displayed to provide a real time indication of hemodynamic and/or thermal-hydraulic parameters within the penis. The measured hemodynamic parameters may be transmitted to a remote terminal for analysis by a remotely located health care professional. Alternatively, the measured hemodynamic parameters may be analyzed by an expert system located either remotely or with the patient.

The present invention is also directed toward an apparatus for stimulating hemodynamic activity within a penis. The apparatus of the present invention comprises an ultrasound generator, and a portable housing coupled to the ultrasound generator. The housing comprises at least one ultrasound trigger and a lower transducer mounting assembly. The invention further comprises an axial position adjuster coupled to the lower transducer mounting assembly and an upper transducer mounting assembly mounted above and in alignment with the lower transducer mounting assembly. The upper transducer mounting assembly is coupled to the axial position adjuster.

A lower ultrasound emitter is mounted in the lower transducer mounting assembly. The lower ultrasound emitter is connected to the ultrasound trigger and to the ultrasound generator. An upper ultrasound emitter is mounted in the upper transducer mounting assembly. The upper ultrasound emitter is connected to the ultrasound trigger and to the ultrasound generator. The apparatus of the present invention may also be used to ultrasonographically measure one or more penile hemodynamic parameters.

DESCRIPTION OF THE PREFERRED EMBODIMENTS

Figure 2:
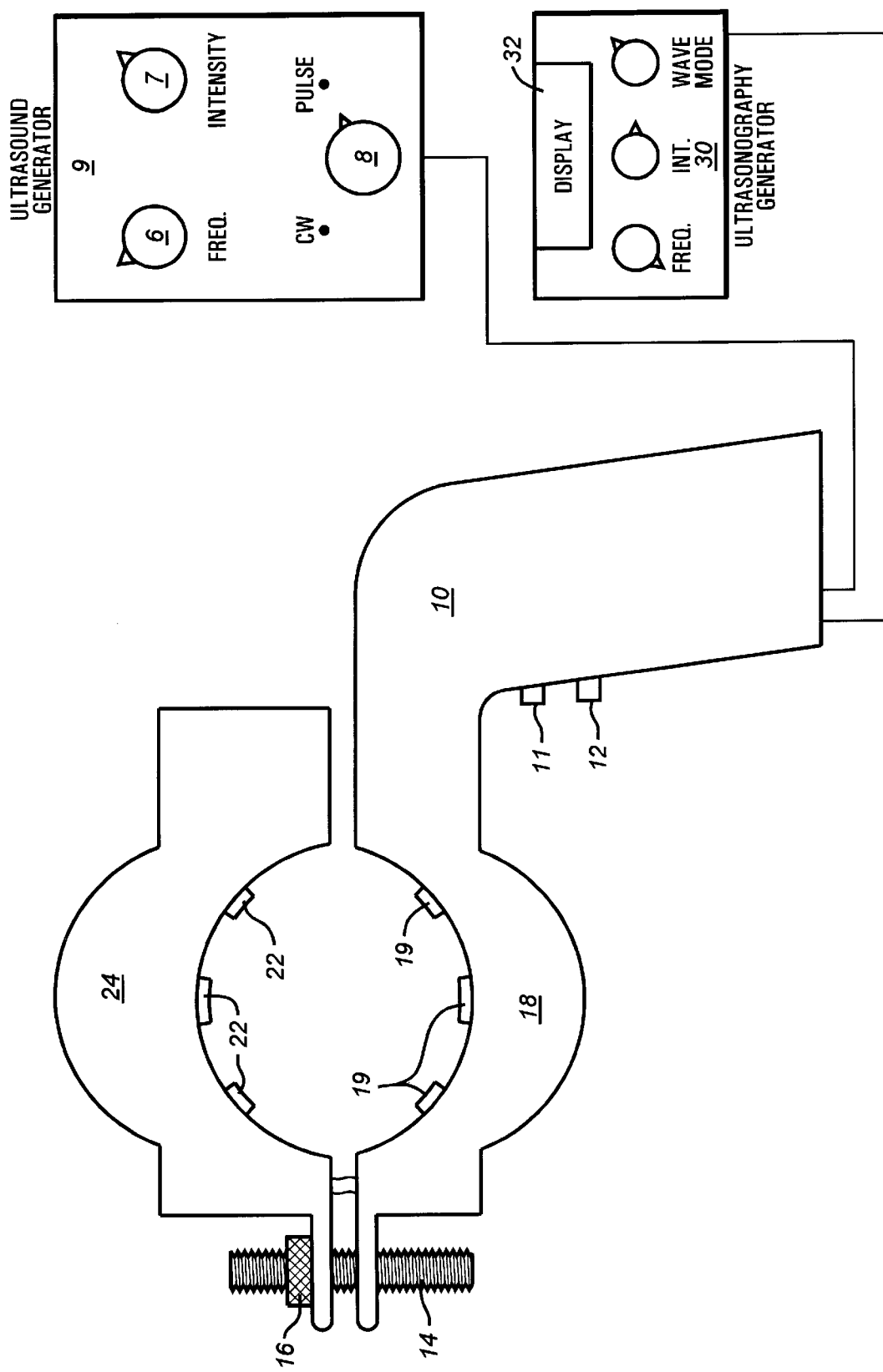
FIG. 2 is a side view of a first apparatus embodiment of the present invention.

The apparatus of the present invention comprises an ultrasound generator 9 and a portable housing 10 coupled to the ultrasound generator, as shown in FIG. 2. The portable housing comprises at least one ultrasound trigger 11 and a lower transducer mounting assembly 18. In a preferred embodiment, the lower transducer mounting assembly is curved.

In a preferred embodiment, the ultrasound generator is capable of selectively generating pulsed or continuous wave ultrasound energy. This selective generation may be accomplished by a control knob or switch 8, as shown in FIG. 2. In a preferred embodiment, the ultrasound generator further comprises frequency controls 6 and intensity controls 7, as shown in FIG. 2.

Figure 4:
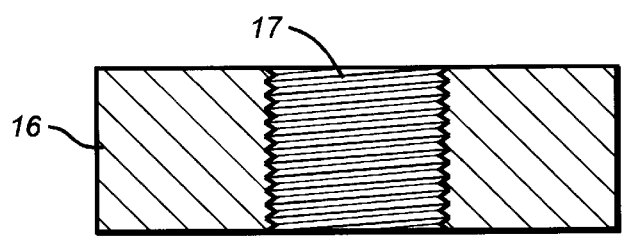
FIG. 4 is a side cross sectional view of the rotatable adjusting wheel of the present invention.

An axial position adjuster is coupled to the lower transducer mounting assembly. In the preferred embodiment shown in FIGS. 2 and 4, the adjuster comprises a threaded rod 14 and a rotatable adjusting wheel 16, comprising a centrally located female threaded channel 17. The channel threadably engages the rod such that when the wheel is rotated, the rod is axially displaced.

It is known in the ultrasound arts that a satisfactory ultrasound coupling is necessary for effective delivery of ultrasound energy to a patient for therapeutic or diagnostic purposes. The axial position adjuster provides a mechanism for maintaining a satisfactory ultrasound coupling as the penis expands circumferentially as a result of increased hemodynamic activity. The axial position adjuster also makes the present invention suitable for use with different patients having varied physical sizes.

The apparatus and method of the present invention may be practiced by the patient, after proper training, without assistance from another person. In the preferred embodiment shown in FIG. 2, the portable housing has a pistol type grip, thereby allowing the patient to operate the trigger or triggers with one hand, while manipulating the axial position adjuster with the other hand as needed to maintain a suitable ultrasound coupling during penile expansion. The placement of the triggers and axial position adjuster on opposite sides of the housing facilitates the patient's ability to comfortably use both hands to simultaneously manipulate the trigger and axial position adjuster.

The invention further comprises an upper transducer mounting assembly 24 mounted above, and in alignment with, the lower transducer mounting assembly. In a preferred embodiment, the upper transducer mounting assembly is curved. The upper transducer mounting assembly is coupled to the axial position adjuster. The radii of curvature of the upper and lower transducer mounting assemblies are sized such that the upper and lower transducers can be coupled to the outer surface of a penis. As shown in FIG. 2, the apparatus of the present invention does not comprise an enclosure that isolates the penis from ambient conditions. Accordingly a penis inserted between the upper and lower transducer mounting assemblies will be exposed to ambient pressure conditions.

A lower ultrasound emitter 19 is mounted in the lower transducer mounting assembly. The lower emitter is connected to the ultrasound trigger and to the ultrasound generator. Electrical and/or electronic circuitry suitable for connecting ultrasound transmitters to an ultrasound generator are described in the following U.S. patents: U.S. Pat. No. 3,735,756 to Richards; U.S. Pat. No. 5,578,060 to Pohl et al.; and U.S. Pat. No. 4,484,569 to Driller et al. The full disclosures of these U.S. patents is incorporated herein by reference.

An upper ultrasound emitter 22 is mounted in the upper transducer mounting assembly, as shown in FIG. 2. The upper ultrasound emitter is connected to the ultrasound trigger and to the ultrasound generator. In a preferred embodiment, the upper and lower ultrasound emitters comprise a multiplicity of transducers, as shown in FIG. 2.

Figure 3:
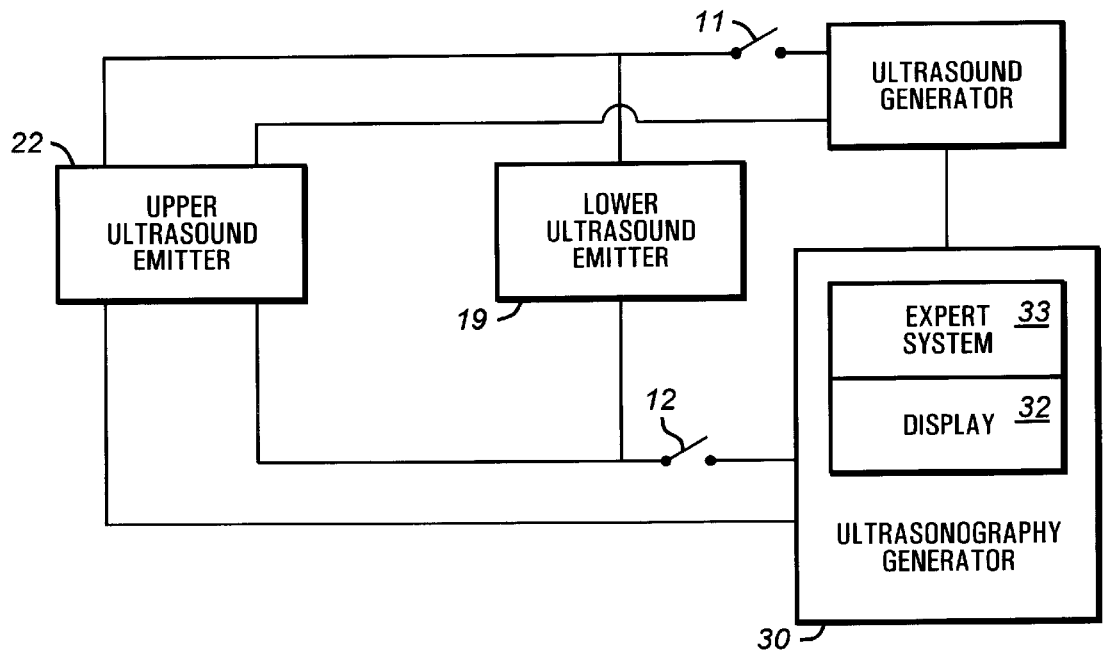
FIG. 3 is a block diagram of a second apparatus embodiment of the present invention.

In the preferred embodiment shown in FIGS. 2–3, the invention further comprises an ultrasonography generator 30 connected to at least one transducer in each transducer mounting assembly and an ultrasonography trigger 12 mounted in the portable housing and connected to the ultrasonography generator. In a preferred embodiment the ultrasonography generator and the ultrasound generator are each connected to at least two ultrasound transducers in each of the transducer mounting assemblies.

The ultrasonography generator is suitable for monitoring penile hemodynamic parameters, such as blood flow. Ultrasonographic apparatus suitable for use with the present invention are disclosed in the following U.S. patents: U.S. Pat. No. 4,612,937 to Miller; and U.S. Pat. No. 4,334,543 to Fehr. The full disclosures of these two patents are incorporated herein by reference. The ultrasonography generator may comprise a display 32 for displaying measured hemodynamic parameters and/or an expert system 33 capable of analyzing measured hemodynamic parameters. The expert system is capable of comparing one or more measured hemodynamic parameters to preestablished parameter limits, such as maximum blood pressure. The expert system is further capable of generating an instruction to the user to stop ultrasound therapy if the predetermined limits are exceeded. These instructions can be generated via the display on the ultrasonography generator or other visual or audible means of communication.

In another preferred embodiment, the expert system is capable of generating an open circuit signal to the ultrasound generator in the event that preestablished limits are exceeded for selected hemodynamic parameters. In this embodiment, the expert system functions as a control circuit for the ultrasound generator.

In a preferred embodiment, measured hemodynamic parameters may also be transmitted to a remote location by a variety of data transmission means, including telephone lines and wireless communication. Transmission to remote location may permit active participation of a health care professional while the patient practices the method of the present invention.

Figure 1A:
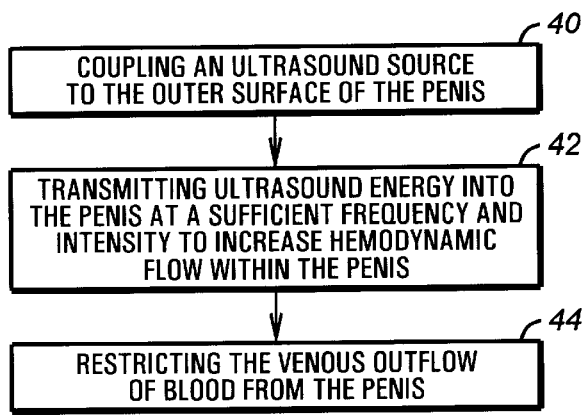
FIG. 1A is a block diagram of a first method embodiment of the present invention.
Figure 1B:
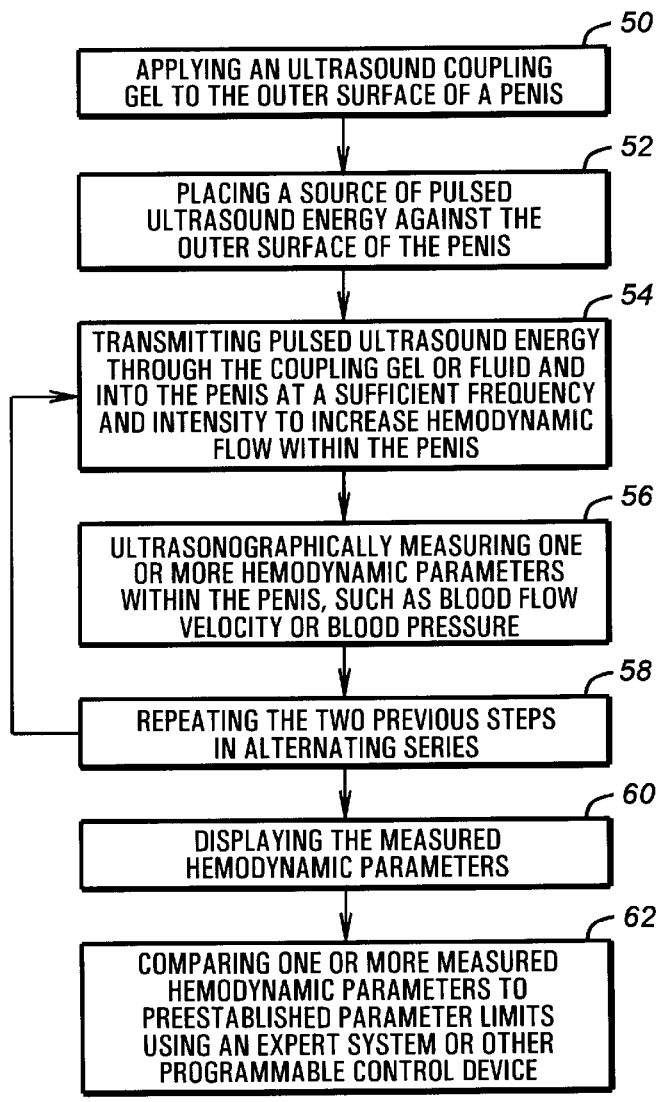
FIG. 1B is a block diagram of a second method embodiment of the present invention.

The present invention also provides a method for stimulating hemodynamic activity within a penis, as shown in FIGS. 1A–1B. The method comprises coupling an ultrasound source to the outer surface of a penis, as shown in block 40 of FIG. 1A. In a preferred embodiment the source of ultrasound energy comprises at least two ultrasound transducers, placed on opposite sides of the penis, as shown in FIG. 2. In another preferred embodiment the source of ultrasound energy comprises a portable housing comprising the transducers.

The method further comprises transmitting ultrasound energy into the penis at a sufficient frequency and intensity to increase hemodynamic flow within the penis, as shown in block 42 of FIG. 1A. The transmission of ultrasound energy may be either pulsed or continuous. In a preferred embodiment the invention further comprises restricting the venous outflow of blood from the penis, as shown in block 44 of FIG. 1A.

Another embodiment of the method invention is shown in FIG. 1B. In this embodiment an ultrasound coupling gel or fluid is applied to the outer surface of a penis, as shown in block 50 of FIG. 1B. A source of pulsed ultrasound energy is placed against the outer surface of the penis, as shown in block 52 of FIG. 1B. The method further comprises transmitting pulsed ultrasound energy through the coupling gel or fluid and into the penis at a sufficient frequency and intensity to increase hemodynamic flow within the penis, as shown in block 54 of FIG. 1B. The next step of the method of this embodiment of the invention is ultrasonographically measuring one or more hemodynamic parameters within the penis, as shown in block 56 of FIG. 1B.

In a preferred embodiment the ultrasonographic measuring comprises a measurement of blood flow velocity. In another preferred embodiment the transmitting and measuring steps are repeated in alternating series, as shown in block 58 of FIG. 1B. In a preferred embodiment, the invention further comprises displaying said measured hemodynamic parameters, as shown in block 60 of FIG. 1B. In another preferred embodiment, the invention comprises comparing one or more measured hemodynamic parameters to preestablished parameter limits, as shown in block 62 of FIG. 1B. This comparison may be performed with an expert system comprising a memory containing preestablished parameter limits. Other programmable controllers known in the instrumentation and control arts may be used to accomplish the comparison step depicted in block 62 of FIG. 1B. The comparison step may be used to provide an input to a control circuit used to control the ultrasound generator.

The embodiments of the invention disclosed herein are illustrative and explanatory. Various changes in size, shape, material, as well as in the details of construction illustrated herein may be made without departing from the scope of the invention.

What is claimed is:

1. A method for injecting ultrasound energy into a penis comprising:

a. coupling an ultrasound source to the outer surface of a penis, said source comprising a lower transducer mounting assembly and an upper transducer mounting assembly mounted above and in alignment with said lower transducer mounting assembly, each of said mounting assemblies comprising one or more transducers, and an axial position adjuster connecting said assemblies, said adjuster being capable of adjusting the distance between said mounting assemblies; and b. transmitting ultrasound energy into the penis.

2. The method of claim 1, further comprising restricting the venous outflow of blood from the penis.

3. The method of claim 1, wherein said transmitting comprises transmitting pulsed ultrasound energy.

4. The method of claim 1, wherein said coupling comprises:

a. applying a coupling gel or fluid to the exterior of the penis; and b. placing said transducers against the portion of said penis on which said coupling gel or fluid has been applied.

5. The method of claim 1 further comprising adjusting the position of the transducers to maintain a satisfactory ultrasound coupling as the penis expands circumferentially.

6. The method of claim 5, wherein said adjusting is performed simultaneously with said transmitting.

7. A method for injecting ultrasound energy into a penis and monitoring hemodynamic activity within a penis comprising:

a. applying an ultrasound coupling gel or fluid to the outer surface of a penis;

b. placing a source of pulsed ultrasound energy against the outer surface of the penis;

c. transmitting pulsed ultrasound energy through said coupling gel or fluid and into the penis; and d. ultrasonographically measuring one or more hemodynamic parameters within the penis.

8. The method of claim 7, further comprising comparing one or more measured hemodynamic parameters to preestablished parameter limits.

9. The method of claim 8, wherein said ultrasonographic measuring comprises a measurement of blood flow velocity or blood pressure.

10. The method of claim 8, further comprising displaying said measured hemodynamic parameters.

11. The method of claim 8 wherein said comparing is performed by an expert system comprising at least one preestablished hemodynamic parameter limit.

12. The method of claim 11 further comprising controlling said transmitting with a control signal produced by said expert system.

13. The method of claim 11 further comprising generating an instruction to the user to stop transmitting when at least one parameter limit is exceeded.

14. The method of claim 7, wherein said ultrasonographically measuring comprises measuring with a set of diagnostic transducers.

15. The method of claim 7, further comprising repeating said transmitting and said measuring in alternating series.

16. A method for monitoring hemodynamic activity within a penis exposed to ambient pressure conditions, comprising:
   a. coupling an ultrasound source to the outer surface of a penis exposed to ambient pressure conditions; and
   b. transmitting ultrasound energy into a penis exposed to ambient pressure conditions; and
   c. ultrasonographically measuring one or more hemodynamic paramaters within the penis exposed to ambient pressure conditions.

17. The method of claim 16 further comprising:
   a. comparing at least one hemodynamic parameter to at least one preestablished parameter limit;
   b. generating a control signal based upon said comparison; and
   c. controlling said transmitting with said control signal.

* * * * *